United States Patent [19]

Larkin

[11] Patent Number: 4,608,043

[45] Date of Patent: Aug. 26, 1986

[54] I.V. FLUID STORAGE AND MIXING SYSTEM

[75] Inventor: Mark E. Larkin, Lindenhurst, Ill.

[73] Assignee: Abbott Laboratories, North Chicago, Ill.

[21] Appl. No.: 623,066

[22] Filed: Jun. 22, 1984

[51] Int. Cl.[4] .......... A61M 5/00

[52] U.S. Cl. .......... 604/87; 206/219; 604/410

[58] Field of Search .......... 604/82, 87–89, 604/92, 56, 262, 408–410; 206/219; 366/130

[56] References Cited

U.S. PATENT DOCUMENTS

| | | | |
|---|---|---|---|
| 2,895,475 | 7/1959 | Cole | 604/87 X |
| 3,030,955 | 4/1962 | Gossett et al. | 604/282 X |
| 3,608,709 | 9/1971 | Pike | 206/219 |
| 3,756,389 | 9/1973 | Firth | 206/219 |
| 3,983,994 | 10/1976 | Wyslotsky | 206/219 |
| 4,458,811 | 7/1984 | Wilkinson | 206/219 |
| 4,496,046 | 1/1985 | Stone | 206/219 |
| 4,568,606 | 10/1985 | Larkin | 604/87 X |

*Primary Examiner*—Dalton L. Truluck

*Attorney, Agent, or Firm*—Michael J. Roth; Alan R. Thiele; Martin L. Katz

[57] ABSTRACT

A system for separately storing and sterilely mixing a diluent and a medicament within a dual chambered flexible container for eventual use in an I.V. administration system. Mixing of the contents of the two chambers is accomplished by compressing the sides of the flexible container thus causing a weakened portion in the partition between the two chambers in the flexible container to rupture, thereby providing fluid communication between the chambers and effecting intermixing of the contents thereof.

5 Claims, 6 Drawing Figures

I.V. FLUID STORAGE AND MIXING SYSTEM

BACKGROUND OF THE INVENTION

This invention relates to a manually operable dual chambered container which includes the means to separately store and sterilely mix the contents of the two chambers by manipulation from outside the container. More particularly, this invention relates to a mixing system for use in the infusion of I.V. liquids. The mixing system is made a part of a single flexible container commonly used to hold a standard liquid diluent such as normal saline solution, dextrose or water. The additive is commonly a powdered or liquid medicament which is compatible with the liquid diluent for treatment purposes but cannot be stored in solution with the liquid diluent for long periods of time.

Container devices providing separate compartments in a single unit for separately enclosing incompatible materials in such a way that they may be later intermixed are described in U.S. Pat. Nos. 2,176,923 to Nitardy, 3,290,017 to Davies, et al., 3,532,254 to Burke, et al. and 3,608,709 to Pike. These container devices are deficient in not being able to maintain an effective fluid-tight seal or moisture barrier between the various spaces formed within the container. This deficiency is caused by the various barriers between the spaces not adequately withstanding the normal rigors of packaging, handling and shipping. If the fluid-tight seal or moisture barrier between the storage spaces is broken, premature mixing of the materials may occur which then renders them ineffective for eventual use. Additionally, for containers used in health care situations, sterility of the materials to be mixed must be strictly maintained. If more complexity is added to the container to assure a fluid-tight seal or moisture barrier between the storage spaces, sequential sterilization of the mixing system during the various stages of manufacture may become difficult and expensive. One solution is to manufacture and fill the container device in a sterile environment. Such manufacture, however, is expensive. Consequently, the need exists in the art to provide a mixing system in a single container which will both provide a fluid-tight seal and an impervious moisture barrier between a powdered medicament and a liquid diluent that can be easily sterilized during manufacture and then conveniently used as the supply portion of an I.V. administration system.

It is therefore an advantage of the present invention to provide a manually operated, storage and mixing system, not subject to the aforementioned and other limitations of the prior art.

It is another advantage of the present invention to provide a manually operable storage and mixing system that is substantially chemically inert, nonbreakable, lightweight, and exceedingly compact.

It is still another advantage of the present container to provide a manually operable, storage and mixing system that does not require special sealing gaskets or "O" rings. Other advantages of the present invention will become more apparent in the following description.

SUMMARY OF THE INVENTION

The container device of the present invention provides a system for separately storing and subsequently mixing in a sterile environment the contents of two chambers formed within a single flexible container. The two chambers are formed by a partition seal which spans the interior of the container. A weakened portion in the partition seal is used to effect fluid communication between one chamber and the other. When it is desired to mix the contents of the two chambers, the chamber holding fluid is compressed so as to cause forces developed within the fluid to sever the weakened portion of the partition seal. Once the weakened portion of the partition seal has been severed, the contents of the two chambers will intermix. Further compression of the walls of the flexible container will cause a flow of fluid from one chamber to the other, thereby agitating the mixture of the contents of the two chambers and completing the mixing process. Dispensing of the mixture from the flexible container is effected by connection of a fluid administration system to the administration port of the container.

DESCRIPTION OF THE DRAWINGS

A better understanding of the storage and mixing device will be had by reference to the drawings wherein.

DESCRIPTION OF THE PREFERRED EMBODIMENT

Figure 2:
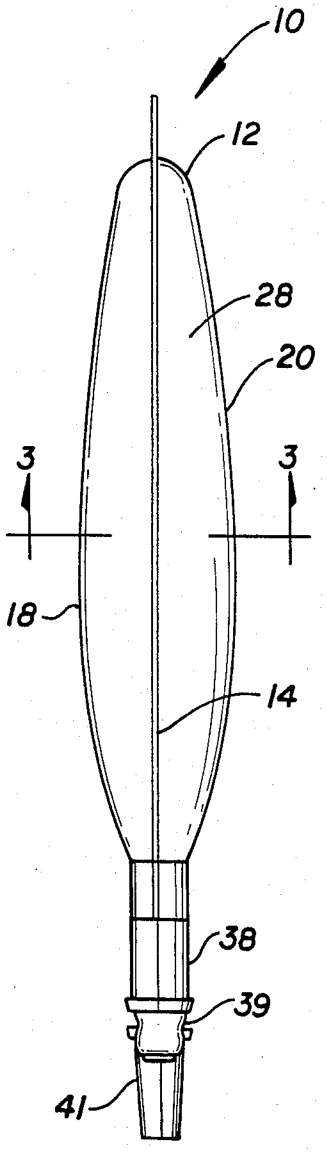
FIG. 2 is a view in side elevation of the storage and mixing device shown in FIG. 1.
Figure 1:
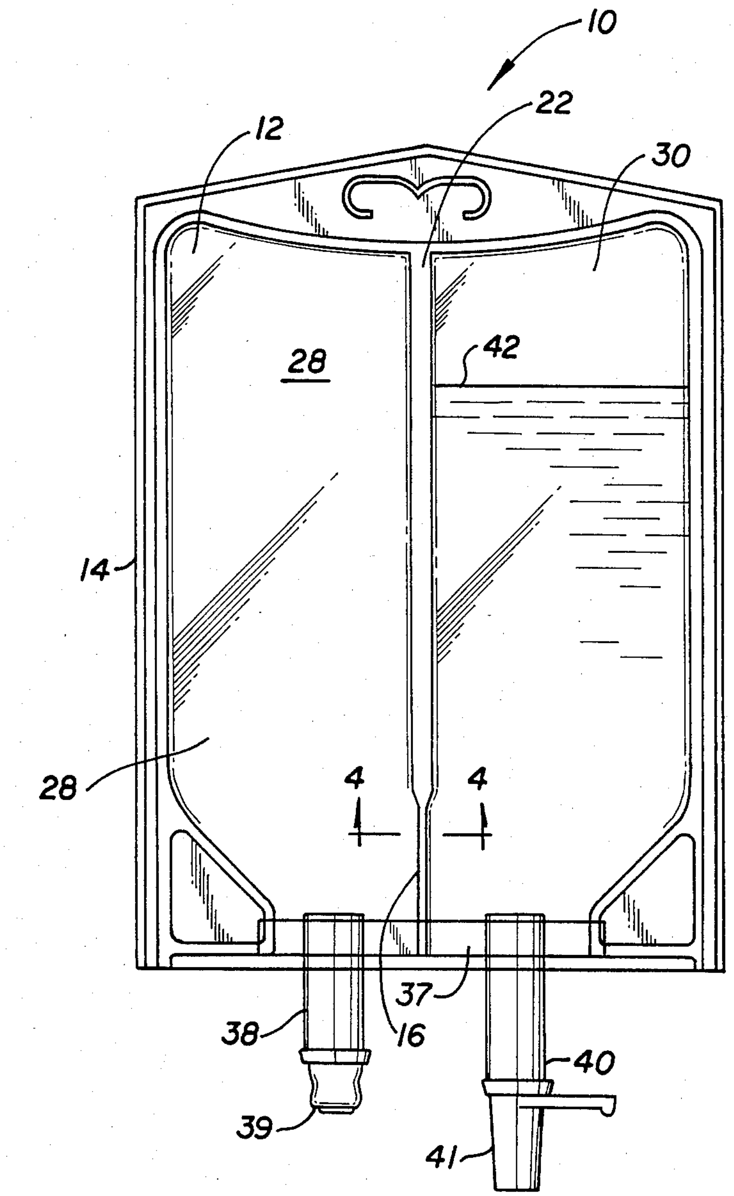
FIG. 1 is a view in front elevation of the storage and mixing device of this invention.
Figure 4:
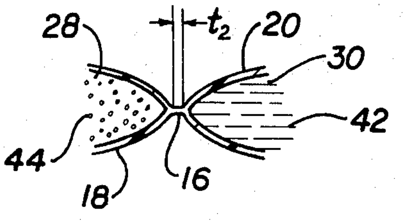
FIG. 4 is a view taken along line 4—4 of FIG. 1.
Figure 3:
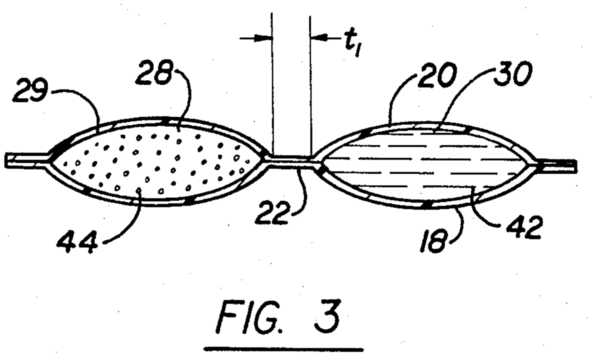
FIG. 3 is a view taken along line 3—3 of FIG. 2.

Proceeding to a detailed description of the preferred embodiment of the invention, the manually operable, storage and mixing container of the present invention, generally 10 shown in FIGS. 1–4 is characterized by having a flexible container 12 formed from two flexible thermoplastic sheets 18 and 20 which are RF welded at their respective perimeters to form edge 14. Flexible sheets 18 and 20 are also RF welded together in their central portion to form a spanning partition 22 which divides the flexible container 12 into two chambers 28 and 30. The partition 22 contains a weakened section 16. An administration port 40 having a cap 41 and an additive port 38 having a rubber reseal 39 and mandrel sealed 37 within edge 14 of the container in fluid communication with chambers 28 and 30 respectively. Liquid 42 and medicament 44 are typically contained within chambers 28 and 30. The chamber 28 containing the medicament 44 may also have an opaque inner liner 29 if the medicament 44 is light sensitive. Weakening of the partition 22 is accomplished by forming a die for RF welding which has a reduced width over a portion of its length. In FIGS. 1 and 3 it is seen that the width of spanning partition 22 is $t_1$ over most of its length and in FIG. 4 it is seen that the width of the weakened portion 16 is $t_2$.

OPERATION

Figure 5:
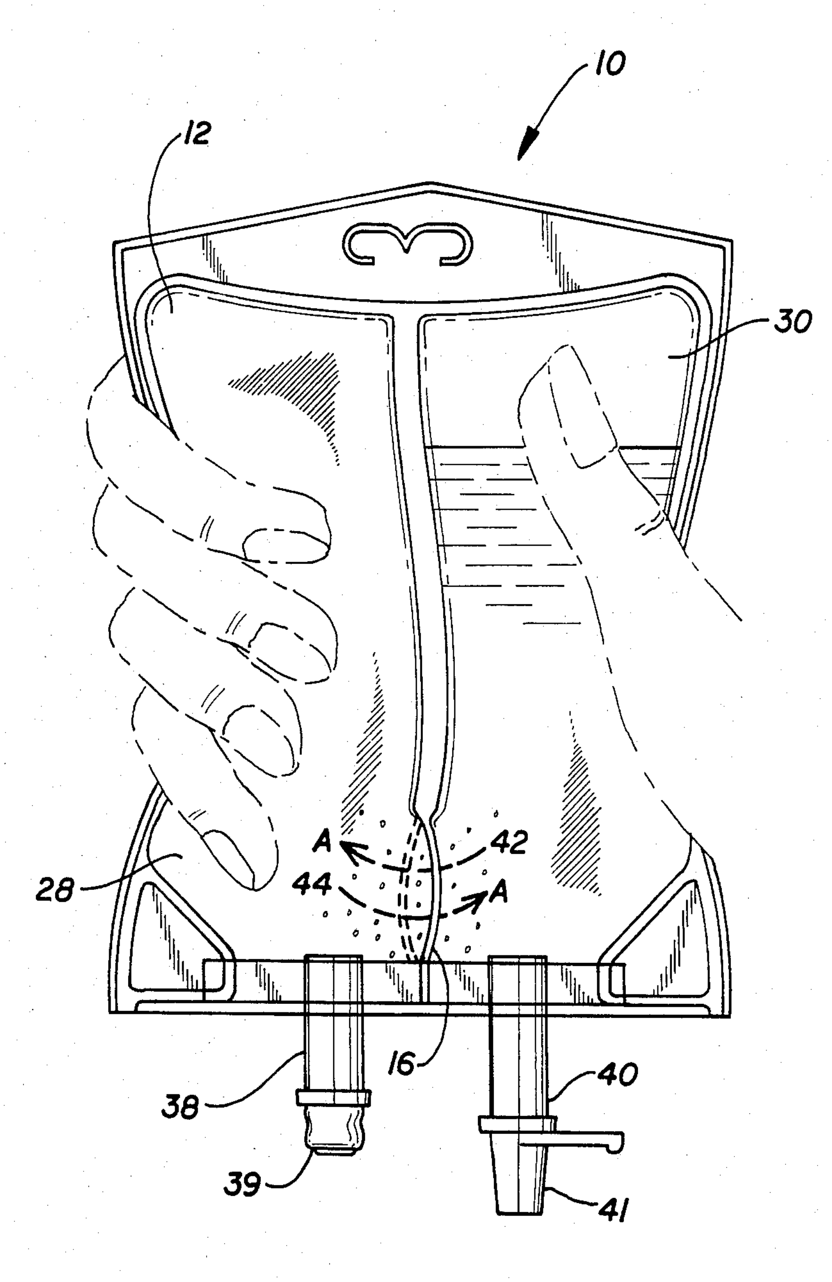
FIG. 5 is a view in front elevation of the storage and mixing device showing its operation.
Figure 6:
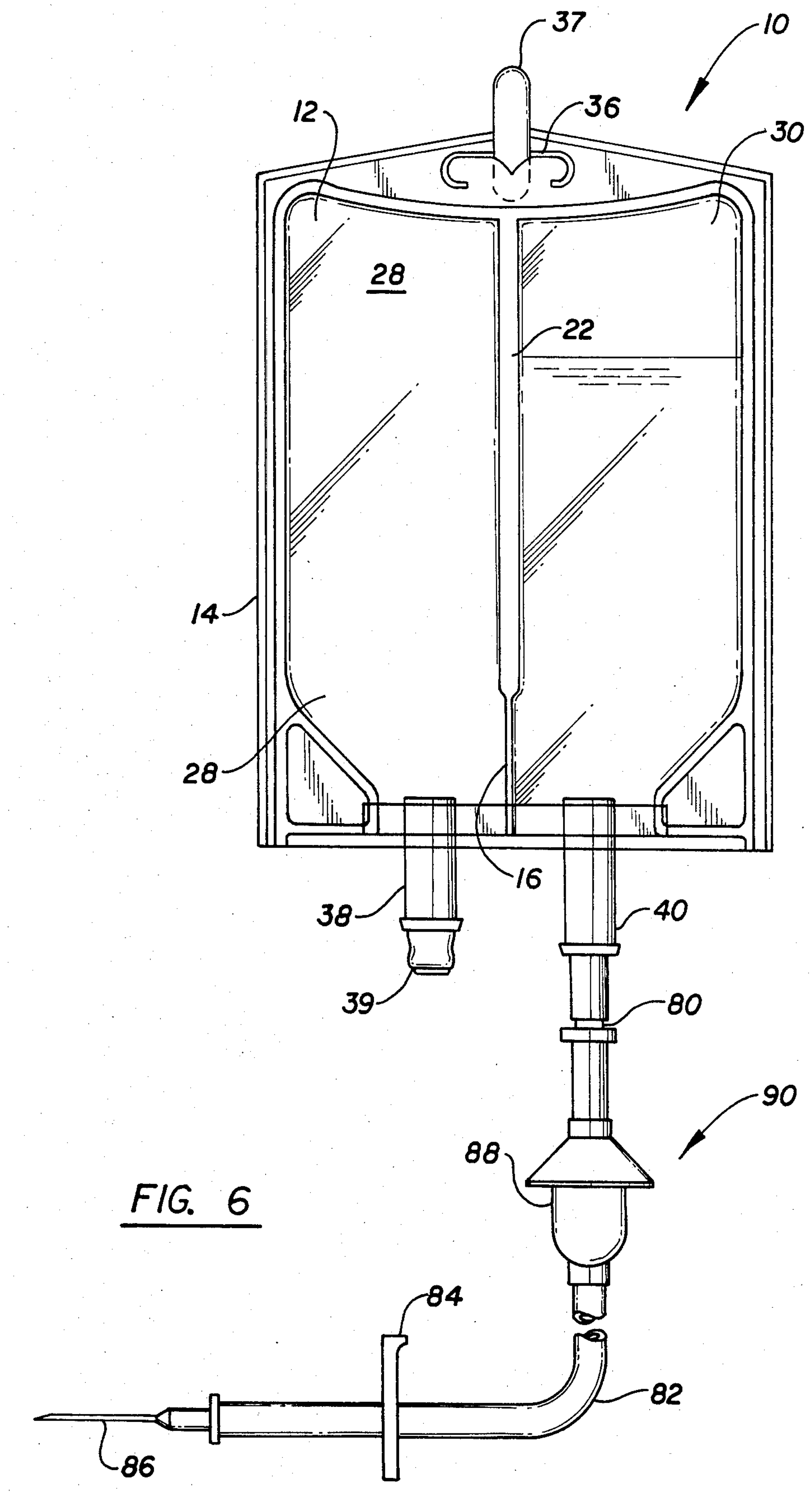
FIG. 6 is a view in front elevation of an intravenous administration system employing the storage and mixing container of this invention.

A further understanding of the advantages of the manually operated storage and mixing system of this invention 10 will become apparent by a descripton of its operation. The dual chambered container 10 will be received by health care personnel generally as shown in FIGS. 1 and 2. As shown in FIG. 5, activation of the device 10 is begun by grasping the flexible container 12. Once grasped, finger and hand pressure may be used to squeeze the flexible outer container 12, thus forcing liquid 42 from its storage chamber 30 against weakened portion 16. Once the weakened portion 16 is broken by the force of the liquid 42, chambers 28 and 30 are in fluid communication. Compression of the sides or the squeezing of the flexible container 12 will cause agitation and mixing of the contents of chambers 28 and 30 as shown by arrows A. As indicated in FIG. 6, once intermixed, the contents of the device 10 may receive further additions or be sampled through additive port 38 and when ready, dispensed into an intravenous administration system, generally 90, through and administration port 40 after removal of the cap 41. Such a system 90 typically consists of a piercing pin 80, flexible tubing 82, a slide on and off clamp 84 and a needle or catheter 86. If desired, a drip chamber 88 may be used to count drops or observe flow. Once the two components 42 and 44 are intermixed, device 10 may be hung by hanger portion 36 from a hook 37 on an I.V. pole (not shown).

The preferred material for manufacturing flexible container 12 of this invention is a translucent polyester or polypropylene plastic material. However, other resinous materials such as polyvinylchloride or polyethylene may be used. The preferred material for the opaque foil lining 29 of the medicament chamber 28 is aluminum foil, however, other suitable materials may be employed.

While the present storage and mixing system has been preferably described for use with a liquid diluent and a powdered medicament, the system may be used with liquids in both chambers. Further, while the present storage and mixing system has been described for use in the health care field, it will be appreciated that the system can be used in other fields. For example, it might have application with other incompatible fluid materials where it is necessary to maintain the two fluid materials in a separately stored and isolated condition until a time just prior to their mixing and use. It should be understood that the term "fluid" as employed in the specification and claims is meant to imply any materials which will flow from one container to another, be it a solid, liquid, or gas.

It will be seen through the present invention there is now provided a storage and mixing system which is easily manufactured and used. The container system of this invention affords a sterile environment for fluid materials of any type during storage as well as mixing, yet in a manner that provides an inexpensive system for the user.

The foregoing invention can now be practiced by those skilled in the art. Such skilled persons will know that the invention is not necessarily restricted to the particular embodiments herein. The scope of this invention is to be defined by the terms of the appended claims, as given meaning by the preceding specification.

What is claimed is:

1. A device for separately storing and subsequently mixing a liquid and a medicament comprising:

a container formed of flexible thermoplastic material and having at least one port;

a partition seal dividing said flexible container, said partition seal spanning the interior of said flexible container to define first and second chambers within said flexible container, the partition seal being formed by a sealing together of opposing walls of the flexible container, said partition seal having at least one weakened section, the weakened section being a section of the partition seal of sufficiently reduced width in comparison to the remainder of the partition seal that the seal in the weakened section will fail under the force of manually generated pressures in the fluid;

said first chamber containing the liquid in fluid communication with said port;

said second chamber containing the medicament;

whereby compressing the walls of said first chamber of the flexible container causes said liquid to rupture the weakened portion of said partition seal and mix the liquid and the medicament.

2. The device as defined in claim 1 wherein said flexible container includes a first port in fluid communication with said first chamber and a second port in fluid communication with said second chamber.

3. The device as defined in claim 2 wherein one of said ports is adapted to receive means for the passage of fluid into an I.V. administration set.

4. The device as defined in claim 1 wherein one chamber contains a liquid diluent and the other chamber contains a powdered medicament.

5. The device as defined in claim 3 wherein the chamber containing powdered medicament has an opaque foil inner lining.

* * * * *